United States Patent [19]

Valle

[11] Patent Number: Plant 6,702

[45] Date of Patent: Mar. 28, 1989

[54] APPLE TREE 'VALLEE SPUR'

[76] Inventor: Jesse E. Valle, HC 11 Box P, Prescott, Wash. 99348

[21] Appl. No.: 78,520

[22] Filed: Jul. 21, 1987

[51] Int. Cl.[4] ..... A01H 5/00
[52] U.S. Cl. ..... Plt./35
[58] Field of Search ..... Plt./35

*Primary Examiner*—James R. Feyrer
*Attorney, Agent, or Firm*—Eugene D. Farley

[57] ABSTRACT

A new variety of Delicious apple tree discovered as a whole tree sport variety of "Red Chief" and characterized by:

(1) Early development of fruit color;
(2) Early development of fruit type;
(3) Early maturity; and
(4) Distinctive "blush" type coloring when ripe.

2 Drawing Sheets

The present invention relates to a new and distinct variety of Delicious apple tree known as "Vallee Spur".

"Vallee Spur" was discovered by Jesse E. Valle on Ralph E. Broetje's Snake River fruit tree ranch located near Fishhook Park, in the southern part of the state of Washington, U.S.A. It was discovered in June of 1984 growing in a block of "Red Chief" Delicious apple trees, as a whole tree sport mutation of "Red Chief". (U.S. Plant Pat. No. 3,578). Since then it has been asexually propagated by bud grafting in the same geographic locality for three generations, during which period its unique characteristics have been shown to be stable and reproduceable.

The unique characteristics of the new apple tree variety "Vallee Spur" are:

1. Early development of fruit color. "Vallee Spur" begins significant color formation early in June; "Red Chief", three or four weeks later.
2. Early development of characteristic apple type. "Vallee Spur" demonstrates typical characteristics early in June; "Red Chief"; three or four weeks later.
3. Distinctive coloring. "Valee Spur" is a blush type apple; "Red Chief", a pronounced stripe.
4. Early maturity. In southern Washington "Vallee Spur" is fully colored, ready to pick from a color stand point by about September 1 each year. By that date it can be picked at optimum maturity with maximum coloring. "Red Chief" is not colored enough to meet Washington State color standards until about the third week of September each year.

These characteristics are illustrated in the accompanying drawings, wherein:

FIGS. 1,2 and 3 are views of Delicious apple tree varieties "Vallee Spur", "Red Chief" and "Early Red One", respectively, all grown in the same orchard in Southern Washington, and all photographed on the same day, i.e. on June 4, 1985. The dramatic early development of color and type by "Vallee Spur", as compared with the other two varieties, is readily apparent.

FIG. 4 is a view of "Vallee Spur" in the same orchard, but taken at a later date in the growing season, i.e. on Aug. 22, 1984. It illustrates the practically complete development of color and type characteristics at that early date. It also illustrates the "blush" (vs. "stripe") color type characteristic of the fruit. For purposes of comparison, a limb of "Red Chief", grown in the same orchard adjacent to the "Vallee Spur" specimen, appears in the background.

FIG. 5 is an enlarged picture of "Vallee Spur", also taken on Sept. 22, 1984, and further illustrating the characteristics and appearance of the mature "Vallee Spur" fruit.

Considering the tree and its fruit in greater detail:

Tree: Tree upright, moderately vigorous, with wide branch angles; semi-dwarf (approximately 75% as large as "Bisbee" strain) at maturity; of intermediate vigor, being less vigorous than some Delicious "spur type" strains (i.e. "Oregon Spur" or "Bisbee" strain) and of vigor similar to its parent.

*Bearing habit.*—"Spur type" tree; annual bearer.

*Trunk.*—Trunk thick, upright, straight, gray color.

*Branches.*—Branches moderately thick, heavy, upright, with wide angles.

*Spurs.*—Spurs strong, closely set, tending to branch.

*Bark.*—Bark grayish in color, smooth on young wood, tending to be moderately "scaley" on older wood.

*Lenticles.*—Lenticles white to gray on present seasons' growth, becoming less prominent with age; on older bark lenticles are gray, cork-like and obscure.

Flowers: Flowers typical of "Red Delicious".

*Pedicle.*—Pedicle strong ($\frac{1}{8}''$ thick), moderate length ($1\frac{1}{4}''$); green at bloom time, changing to irregularly red at harvest.

*Receptacle.*—Receptacle cone shaped, pubescent, light green; fused broadly into sepals.

*Calyx.*—Calyx made up of 5 fused sepals each sharply pointed; pubescent, light green and long ($\frac{3}{8}''$) at bloom time, enlarging rapidly at the base following fertilization to form prominent calyx lobes.

*Petals.*—Petals borne in single row, large, white with some pink toward base.

*Staymens.*—Staymens borne in a single whorl; filament, white; anther full and yellow before pollen shed, turning black, hard and small after pollen shed.

Fruit: fruit large, solid red, with prominent calyx lobes at maturity.

*Skin.*—Skin smooth, glossy, medium thick, with low chlorophyll content at maturity.

*Surface bloom.*—Fruits covered by light surface bloom at harvest; following storage, fruits develop moderate to heavy surface bloom in three to five days at room temperature.

*Color.*—Color sharp, deep uniform red lacking the deep red-on-red stripe color pattern of strains such as "Red Chief", "Oregon Spur" or "Ace"; color development begins in early to mid-June reaching full color two to three weeks ahead of "Red Chief" and up to six weeks ahead of "Bisbee"; color at maturity is uniformly dark red (5R 3/7 Nickerson Color Fan; 1957 edition, published by Munsell Color Co., Inc., Baltimore, Md. and distributed by the American Horticultural Council.)

*Lenticils.*—Lenticils small, white, spaced widely on the shoulders of the fruit, but more closely toward the calyx end.

*Shape.*—Fruits round in cross-section, markedly elongated along the stem-calyx axis with prominent calyx lobes.

*Flesh.*—Flesh white, crisp, mild-flavored, smooth with slight green color in major vascular bundles until fully mature.

I claim:

1. The new and distinct Variety of apple tree "Vallee Spur", substantially as shown and described.

* * * * *

FIG. 1 "VALLEE SPUR"
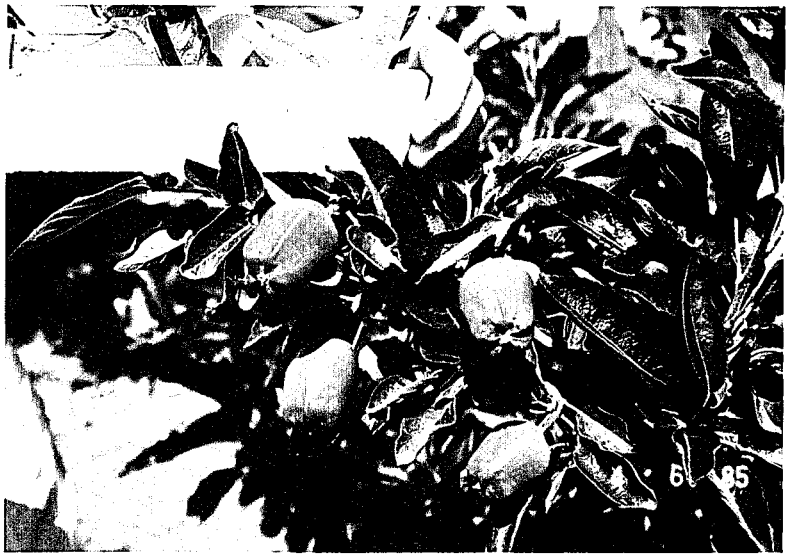
FIG. 2 "RED CHIEF"
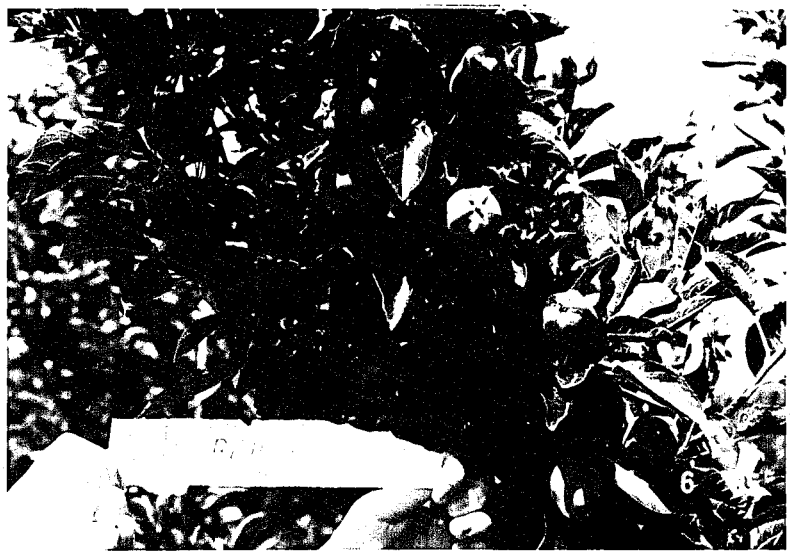
FIG. 3 "EARLY RED ONE"
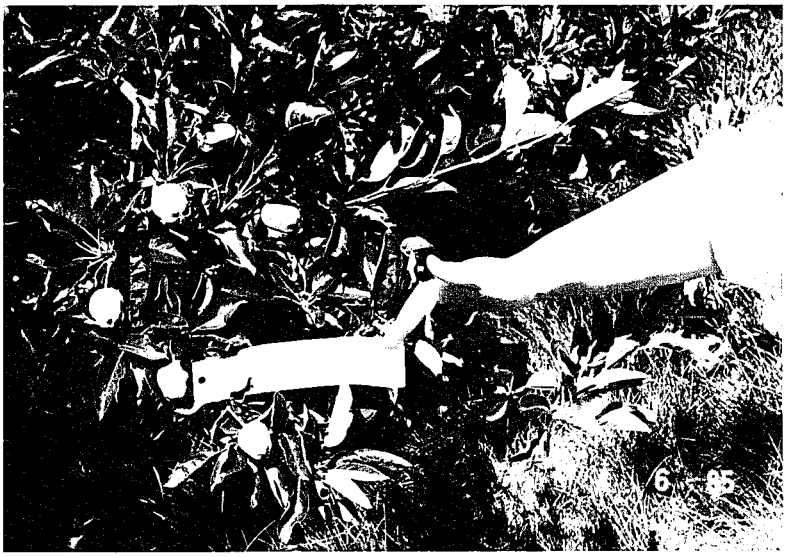

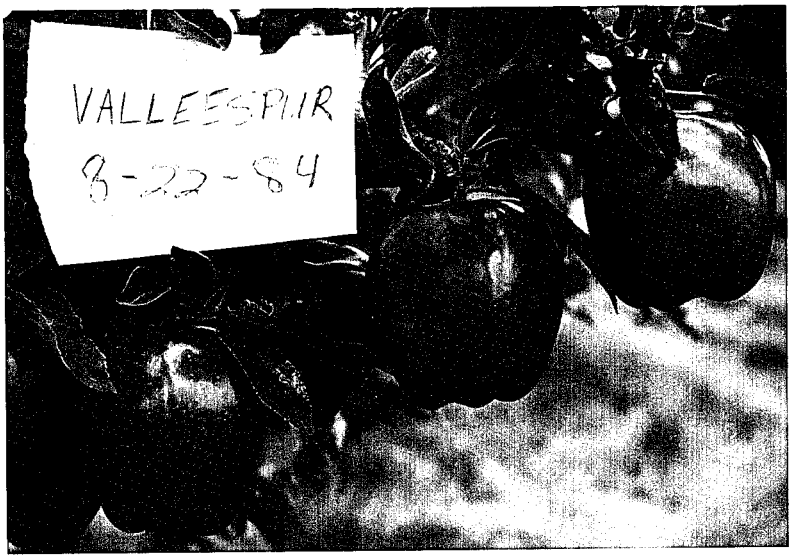

FIG. 4 "VALLEE SPUR"
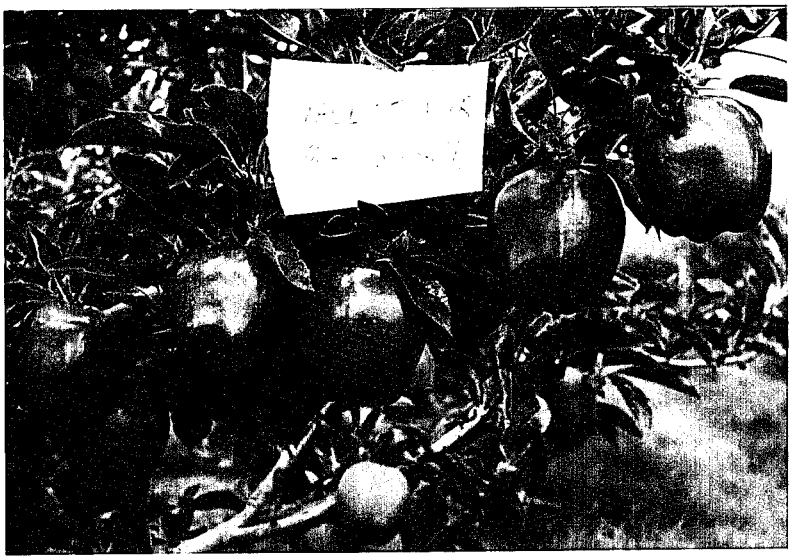
FIG. 5 "VALLEE SPUR"